United States Patent [19]

Gaiser

[11] Patent Number: 4,753,238
[45] Date of Patent: Jun. 28, 1988

[54] PROXIMAL MANIFOLD AND ADAPTER

[75] Inventor: John W. Gaiser, Mountain View, Calif.

[73] Assignee: Advanced Cardiovascular Systems, Inc., Mountain View, Calif.

[21] Appl. No.: 712

[22] Filed: Jan. 6, 1987

[51] Int. Cl.$^4$ ............................................. A61M 29/02
[52] U.S. Cl. ...................................... 128/344; 604/101
[58] Field of Search .................... 128/344, 348.1, 356; 604/96–103, 283, 86

[56] References Cited

U.S. PATENT DOCUMENTS

| | | | |
|---|---|---|---|
| 3,211,150 | 10/1965 | Foderick | 604/99 |
| 3,426,744 | 2/1969 | Ball | 128/344 |
| 4,307,722 | 12/1981 | Evans | 128/344 |
| 4,335,719 | 6/1982 | Johnston | 604/97 |
| 4,641,654 | 2/1987 | Samson et al. | 128/344 |
| 4,655,746 | 4/1987 | Daniels et al. | 128/348.1 |

Primary Examiner—Dalton L. Truluck
Assistant Examiner—Frank Wilkens
Attorney, Agent, or Firm—Fulwider, Patton, Rieber, Lee & Utecht

[57] ABSTRACT

Proximal manifold and adapter device for use with a catheter having first and second lumens. A manifold having a plurality of arms is provided. One of the arms has a passage therein in communication with the first lumen. Another of the arms is in communication with the second lumen. An interconnector connects said first and second arms for establishing communication between the same. The innerconnector means includes a housing having an inlet port and a valve for establishing communication between the inlet port and the side arms.

9 Claims, 2 Drawing Sheets

PROXIMAL MANIFOLD AND ADAPTER

This invention relates to a proximal manifold and adapter and, more particularly, to such a manifold and adapter for use with a tandem balloon dilatation catheter.

Adapters have heretofore been provided for use with balloon dilatation catheters. Adapters, however, have not been available which give individual access to lumens in a single catheter shaft and which can be utilized for performing operations from a single inflation/deflation device for inflating two tandem balloons. There is therefore a need for such a device.

In general, it is an object of the present invention to provide a proximal manifold and adapter which is adapted to be mounted on a catheter shaft carrying a pair of lumens and for performing operations with respect to the pair of lumens.

Another object of the invention is to provide a manifold and adapter of the above character which can be utilized for inflating and deflating tandem balloons from a single inflation/deflation device.

Another object of the invention is to provide a manifold and adapter of the above character which can be utilized for inflating one tandem balloon while the other one is being deflated.

Another object of the invention is to provide a manifold and adapter of the above character which can be readily manufactured.

Another object of the invention is to provide a manifold and adapter of the above character which can be readily operated.

Additional objects and features of the present invention will appear from the following description in which the preferred embodiments are set forth in detail in conjunction with the accompanying drawing.

FIG. 3 is a cross-sectional view taken along the line 3—3 of FIG. 2.

FIG. 4 is a cross-sectional view taken along the line 4—4 of FIG. 2.

Figure 1:
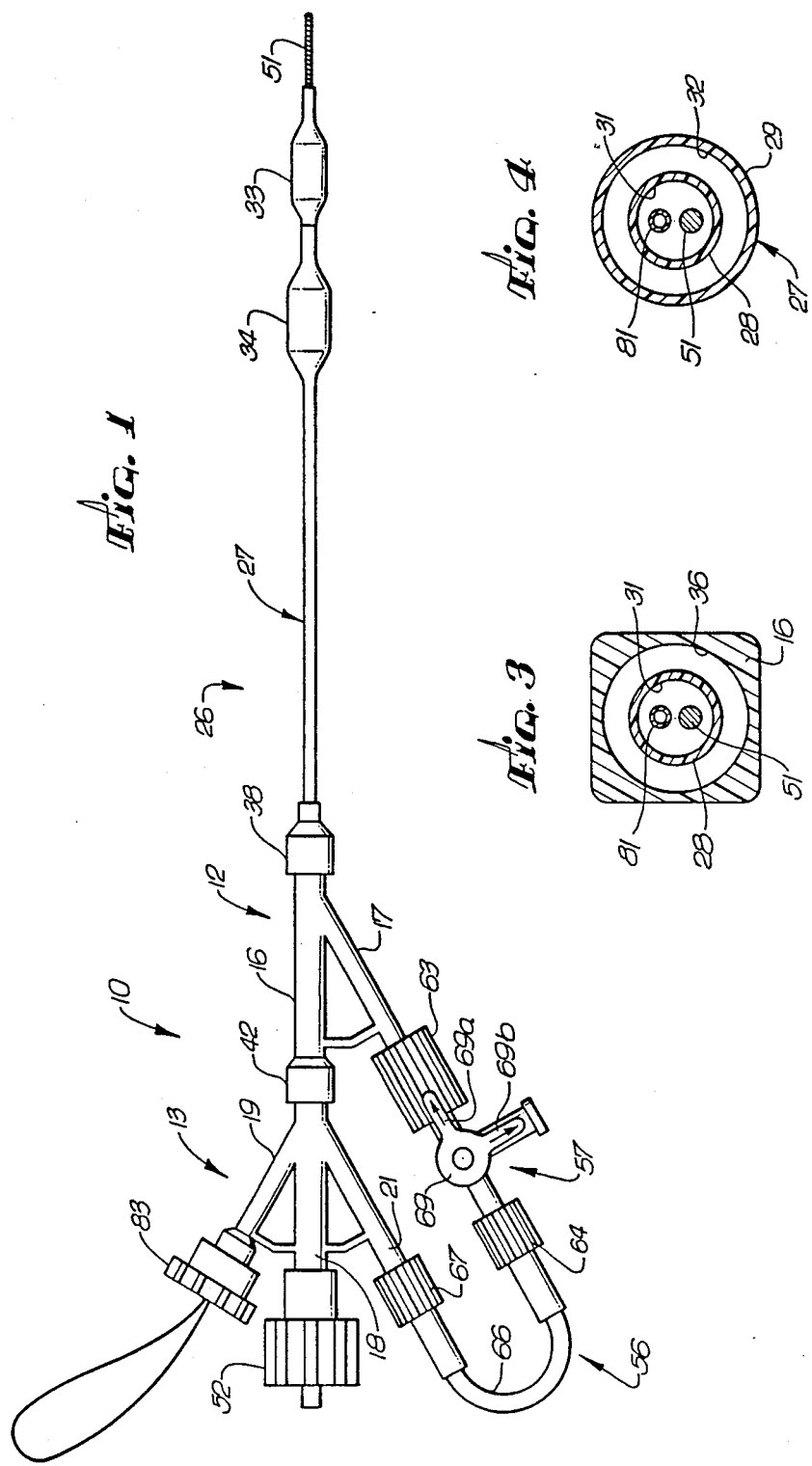
FIG. 1 is a top plan view of a balloon dilatation catheter having a proximal manifold and adapter incorporating the present invention.
Figure 2:
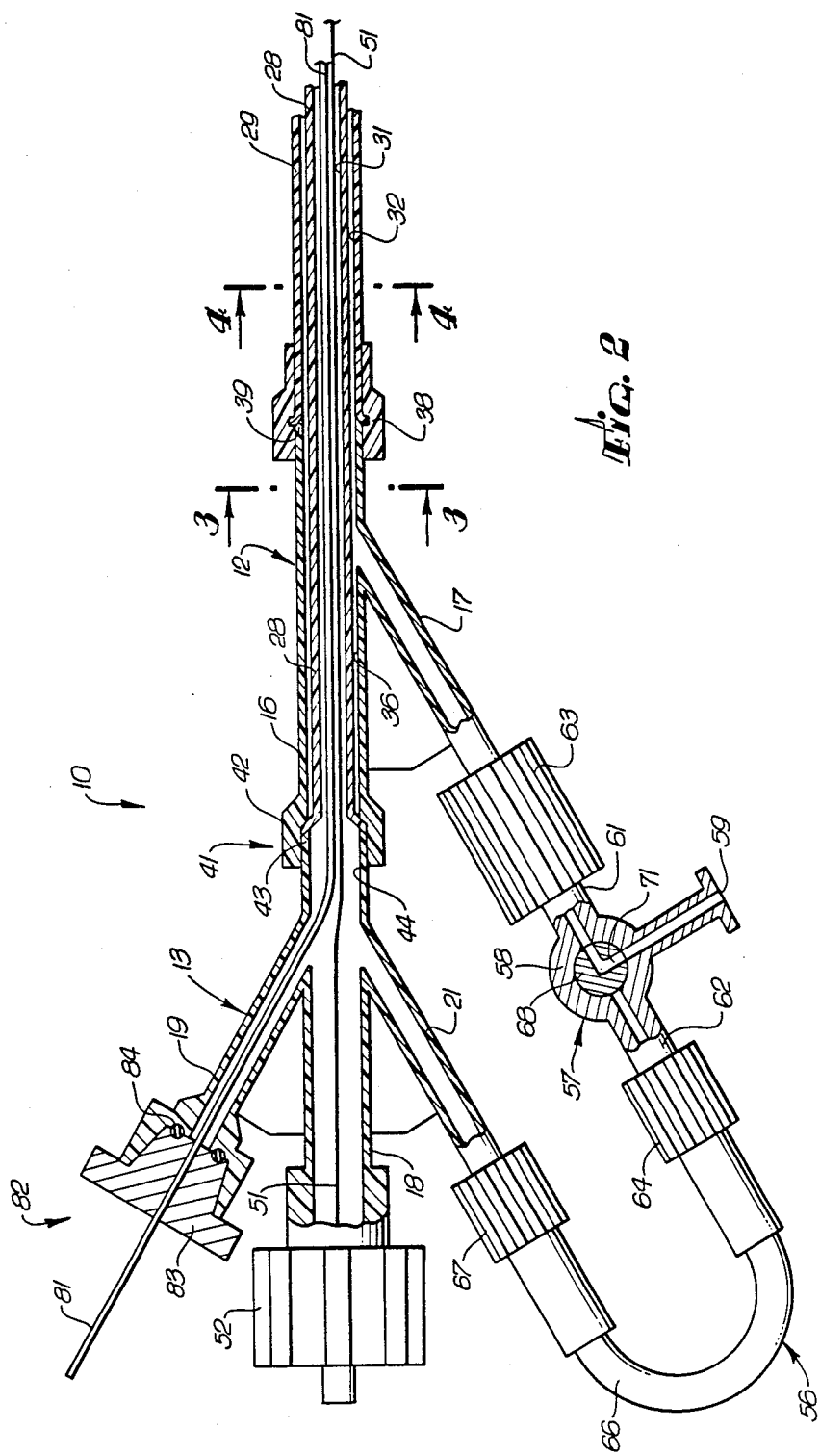
FIG. 2 is a partial cross-sectional view of the proximal manifold and adapter shown in FIG. 1.

In general, the proximal manifold and adapter device is comprised of first and second adapters with each of the adapters having a plurality of arms. Interconnecting means is provided for interconnecting one of the arms of each of the adapters so that they are in series and are adapted to be placed in communication with the first lumen. Additional innerconnecting means is provided for innerconnecting one additional arm of each of the adapters. One of the additional arms of one of the adapters is adapted to be placed in communication with the first lumen and the other one of the additional arms of the other adapter is adapted to be placed in communication with the second lumen. The additional innerconnecting means includes an inlet port and means for selectively connecting the inlet port to either of said additional arms.

More in particular, the proximal manifold and adapter device 10 comprises first and second adapters 12 and 13, each of which includes a plurality of arms. For example, the first adapter 12 is provided with a central arm 16 and a side arm 17 and the second adapter 13 is provided with a central arm 18 and side arms 19 and 21.

The proximal manifold adapter device 10 is adapted to be mounted upon the proximal extremity of a dilatation catheter 26. One particular dilatation catheter particularly suited for use with this device is a tandem balloon dilatation catheter described in copending application Ser. No. 07/000,696 filed 1/6/87 (A-44508). The dilatation catheter 26 includes a shaft in the form of a flexible tubular member 27 which consists of an inner tubular member 28 and an outer tubular member 29 which is co-axially disposed on the inner tubular member 28. A first lumen 31 is provided in the inner tubular member 28 and a second lumen 32 is provided between the exterior wall of the inner tubular member 28 and the interior wall of the outer tubular member 29 in the form of an annular flow passage. The lumens 31 and 32 are in communication with distal and proximal balloons 33 and 34 respectively.

The first adapter 12 is provided with a flow passage 36 in the central arm 16 which is placed in communication with the second lumen 32 by a removable connection formed of a fitting 38 which is threaded onto the distal extremity of the adapter 12 and frictionally urges the proximal extremity of the outer tubular member 29 over a conical tip 39 provided on the distal extremity of the adapter 12. Thus it can be seen that the second lumen 32 is in communication with the side arm 17 of the first adapter 12.

Innerconnecting means 41 is provided for innerconnecting one of the arms of the second adapter 13 to one of the arms of the first adapter 12. Thus as shown in FIG. 1, the central arm 18 is connected in series with the central arm 16. A fitting 42 on the proximal extremity of the central arm 16 of the adapter 12 frictionally urges the proximal extremity of the inner tubular member 28 over a conical tip 43 on the distal extremity of the adapter 13. The adapter 13 is provided with a flow passage 44 which is in communication with the first lumen 31 in the inner tubular member 28. The flow passage 44 also is in communication with the side arm 21.

A core wire 51 of a conventional construction is adapted to be inserted through the first and second adapters 12 and 13 and to extend through the first lumen 31 of the dilatation catheter 26. The guide wire 51 can be of a movable type or, alternatively, as shown in FIG. 1, it can be of the fixed type which cannot be extended and retracted but can be rotated by suitable means such as by a torque knob assembly 52 secured to the proximal extremity of the guide wire 51. The torque knob assembly 52 can be of a type disclosed in U.S. patent application Ser. No. 760,635, filed July 30, 1985, now U.S. Pat. No. 4,664,113 and is provided for limiting the rotation of the guide wire so that it can be rotated no more than approximately 1½ to 2 turns. The torque knob assembly 52 can be utilized for rotating the guide wire through a limited angular rotation, as for example, through 360 degrees to facilitate negotiation of the arterial vessel of the patient.

Additional innerconnecting means 56 is provided for connecting one of the additional arms of the first adapter to another of the other arms of the second adapter 13. The additional innerconnecting means 56 as shown in FIG. 1 connects the arm 17 of the first adapter 12 to the side arm 21 of the second adapter 13. The additional innerconnecting means 56 includes a stop cock assembly 57. The stop cock assembly 57 consists of a housing 58 which is provided with a Luer-type inlet port 59 and Luer-type side ports 61 and 62. The side port 61 is connected to the arm 17 by a Luer-type fitting 63 whereas the Luer-type side port 62 is connected by a Luer-type fitting 64 mounted on one end of a flexible plastic tube 66. Another Luer-type fitting 67 is mounted on the other end of the tube 66 and is connected to the Luer-type side arm 21. The stop cock assembly 57 also includes a rotatable valve member 68 which is provided with a handle 69 for rotating the same. The valve member 68 is provided with an ell-shaped flow passage 71 which is adapted to be moved to establish communication from the inlet port 59 to either of the side ports 61 and 62 or to either one of the side ports 61 and 62 to the exclusion of the other. The inlet port 59 is adapted to be connected to an inflation/deflation device (not shown) of the type described in U.S. Pat. No. 4,439,185. The handle 69 is provided with two wings 69a and 69b which extend at right angles to each other and correspond in positions to the arrangement of the ell-shaped passage 71 and indicate the path of flow through the ell-shaped passage 71.

The other arm 19 of the adapter 13 can be utilized for receiving a vent tube 81 which can be introduced through the passage 44 in the fitting 13 and through the first lumen 31 and into the distal balloon of the tandem balloon. A valve 82 of a conventional type is mounted on the outer end of the arm 19 to prevent fluid flow from the arm 19 with the vent tube 81 in place. It includes a knob 83 which engages an O-ring 84.

Operation and use of the proximal manifold and adapter device 10 may now be briefly described as follows. Let it be assumed that it is desired to utilize the device 10 in connection with a tandem dilatation balloon catheter of the type described in co-pending application Ser. No. 07/000,696, filed 1/6/87 (A-44507). Let it be assumed that the tandem balloon dilatation catheter has been prepared for insertion into the vessel of the patient by first inflating the balloons 33 and 34 outside of the patient and then deflating the same and introducing the same into the vessel of the patient by the use of the guide wire. The balloons 33 and 34 in this condition would both be in deflated conditions by drawing a vacuum on the balloons by having the two-way stop cock assembly 57 positioned in the manner shown in FIG. 1 in which the inlet port 59 is placed in communication with the side port 61 through passage 71 and thereafter in a position rotated by 90°. The inlet port 59 is placed in communication with the side port 62 through passage 71 and the second lumen 31 which is in communication with the proximal balloon, or in other words, the larger balloon 34. The valve member 68 is then rotated through 90° in a clockwise direction so that the inlet port 59 is in communication with the side port 62 and the first lumen 31 which is in communication with the distal balloon, or in other words, the smaller balloon 33.

The dilatation catheter 26 is placed in the vessel of the patient in a conventional manner. The deflated distal balloon 33 is then positioned in the stenosis. After it has been positioned in the stenosis, it can be inflated by the inflation deflation device for an appropriate period of time. (Inlet port 59 is in communication with side arm 62 and first lumen 31.) The balloon 33 is then deflated by use of the inflation/deflation device. The valve member 68 is then rotated through 90° so that the inlet port 59 is in communication with the side arm 61 and the second lumen 32. The proximal balloon 34 is then positioned in the stenosis. The proximal balloon 34 can then be inflated by an inflation deflation device by introducing a radiopaque contrast liquid through the port 59. After the inflation has continued for an appropriate interval of time, the balloon 34 is deflated and the tandem balloon dilatation catheter 26 can be removed from the patient's vessel.

It can be seen from the foregoing procedure that only a single inflation-deflation device was utilized for inflating and deflating the tandem balloons 33 and 34. The proximal manifold adapter device 10 has numerous advantages in that it makes it possible to inflate and deflate tandem balloons by the use of a single inflation and deflation device. This greatly simplifies the procedures and the amount of equipment needed for an angioplasty procedure. The use of the three-way stop cock assembly 57 makes possible the simplified operation with the use of only a single inflation and deflation device.

In conjunction with the foregoing construction it should be appreciated that in place of the first and second adapters 12 and 13 forming a manifold, a single molded part can be produced for the manifold to reduce the size and complexity of the device, while still making it possible to obtain the necessary arms to obtain access to the various lumens of the dilatation catheter. It also should be appreciated that if additional lumens are desired to be accessed, the two-way stop cock assembly 57 can be replaced with a three-way stop cock assembly to allow access to a third lumen. It also should be appreciated that although the foregoing construction has been described in connection with a catheter construction utilizing co-axial or concentric lumens, that the desired lumens could be provided in an extruded flexible tubular member with the lumens being placed side by side in the same tubular member.

What is claimed is:

1. A proximal manifold and adapter device in combination with a dilatation catheter having a first lumen in fluid communication with a first balloon on the distal portion of the catheter and a second lumen in fluid communication with a second balloon on the distal portion of the catheter, a manifold having a plurality of arms with fluid flow passage therein, one of the arms having a passage therein in communication with the first lumen, another of the arms having a passage therein in communication with the second lumen, and means interconnecting said first and second arms in fluid communication therebetween, said interconnecting means including a housing having an inlet port, discharge ports in fluid communication with said arms, and valve means intermediate said discharge ports for establishing fluid communication between the inlet port and the said arms through the discharge ports.

2. A device as in claim 1 wherein said manifold includes first and second adapters, each of said adapters being provided with a plurality of arms.

3. A device as in claim 1 wherein said valve means is provided with a flow passage.

4. A device as in claim 3 wherein the flow passage is ell-shaped.

5. A proximal manifold and adapter device in combination with a dilatation catheter having first and second lumens in fluid communication with first and second balloons on the distal portion of the catheter, first and second adapters having a plurality of arms with fluid flow passages therein, means interconnecting in fluid communication one arm of each of the adapters so that they are in series and adapted to be placed in fluid communication with the first lumen, additional means interconnecting in fluid communication one additional arm of each adapter, said additional interconnecting means including an inlet port, discharge ports in fluid communication with said additional arms, and valves means intermediate said discharge ports for connecting in fluid communication said inlet port selectively to either one of said arms.

6. A device as in claim 4 wherein said valve is a two-way valve.

7. A device as in claim 9 wherein said valve is provided with a ell-shaped flow passage.

8. A device as in claim 5 wherein the valve means is a two-way valve.

9. The device as in claim 5 wherein the valve means is provided with a flow passage.

* * * * *